United States Patent [19]

Waitz et al.

[11] Patent Number: 4,735,903

[45] Date of Patent: Apr. 5, 1988

[54] MICROMONOSPORA CARBONACEA VAR AFRICANA

[75] Inventors: Jay A. Waitz, Portola Valley, Calif.; Ann C. Horan, Summit, N.J.

[73] Assignee: Schering Corporation, Kenilworth, N.J.

[21] Appl. No.: 845,094

[22] Filed: Mar. 27, 1986

Related U.S. Application Data

[60] Division of Ser. No. 623,266, Jun. 21, 1984, Pat. No. 4,597,968, which is a continuation-in-part of Ser. No. 405,822, Aug. 6, 1982, abandoned.

[51] Int. Cl.$^4$ .......................... C12N 1/20; C12P 1/04; C12R 1/29

[52] U.S. Cl. .................... 435/253; 435/170; 435/867

[58] Field of Search .............. 435/170, 253, 867

[56] References Cited

PUBLICATIONS

Sattler, A. et al.; 'The Everninomicins Biosynthetic Studies'; *Journal of Antibiotics*, Apr. 1970, v. 23, N. 4, pp. 210–215.

*Primary Examiner*—Elizabeth Weimar
*Attorney, Agent, or Firm*—Thomas D. Hoffman; Gerald S. Rosen

[57] ABSTRACT

A new variety of *Micromonospora carbonacea*, namely *Micromonospora carbonacea* var *africana* NRRL 15099, ATCC 39149.

1 Claim, 10 Drawing Sheets

TIME COURSE STUDY OF 13-384 FERMENTATION $^1$H NMR SPECTRUM OF ANTIBIOTIC 13-384 COMPONENT I

13C NMR SPECTRUM OF ANTIBIOTIC 13-384 COMPONENT I

U.V. SPECTRA OF ANTIBIOTIC 13-384
COMPONENT 5

$^1$H NMR SPECTRUM OF ANTIBIOTIC 13-384 COMPONENT 5

HPLC OF 13-384 FERMENTATION BROTH

MICROMONOSPORA CARBONACEA VAR AFRICANA

CROSS REFERENCE TO RELATED APPLICATION

This application is a divisional application of U.S. patent application Ser. No. 623,266, filed June 21, 1984, now U.S. Pat. No. 4,597,968 which is a continuation-in-part application of U.S. patent application Ser. No. 405,822, filed Aug. 6, 1982, now abandoned.

BACKGROUND OF THE INVENTION

This invention relates to a new antibiotic complex elaborated by a novel variety of *Micromonospora carbonacea*. More particularly, this invention relates to antibiotic 13-384 complex produced in a fermentation under controlled conditions using a biologically pure culture of the new microorganism, *Micromonospora carbonacea* var *africana* var nov. NRRL 15099, ATCC 39149.

SUMMARY OF THE INVENTION

The present invention embraces *Micromonospora carbonacea* var *africana* NRRL 15099 and mutants and variants thereof having the distinguishing characteristics of *Micromonospora carbonacea* var *africana* NRRL 15099.

Thus, in one of its aspects, this invention is directed to producing the antibiotic 13-384 complex which comprises cultivating *Micromonospora carbonacea* var *africana* NRRL 15099 in an aqueous nutrient medium containing assimilable sources of carbon and nitrogen, under aerobic conditions until substantial antibiotic activity is imported to said medium and isolating antibiotic 13-384 complex therefrom.

The present invention is also directed to the novel antibiotic 13-384 complex, and to the components 1 and 5 thereof and to the pharmaceutically acceptable salts thereof.

The present invention is also directed to the use of antibiotic 13-384 complex or components thereof as antibacterial agents.

ISOLATION AND PURIFICATION OF THE ANTIBIOTIC COMPLEX

Figure 1:
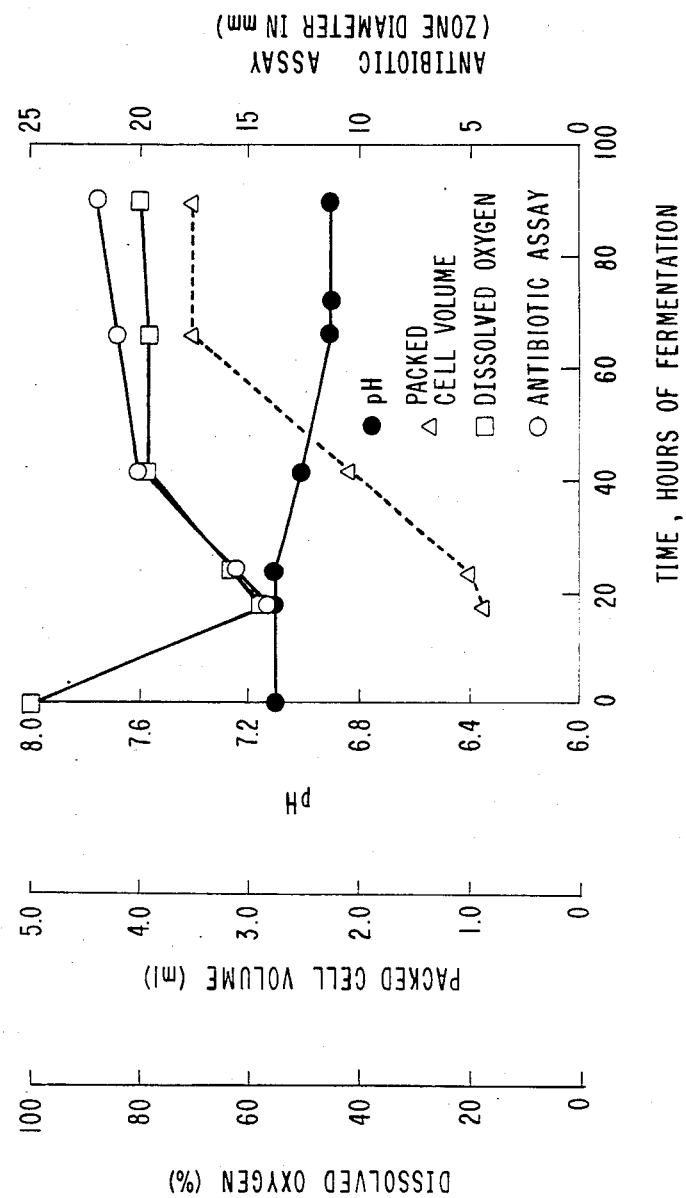
FIG. 1 graphically illustrates a time course study of 13-384 fermentation against several parameters.

Antibiotic 13-384 complex is produced when the elaborating organism, *Micromonospora carbonacea* var *africana*, var nol NRRL 15099, is grown in an appropriate nutrient medium.

Antibiotic 13-384 complex may be isolated from the fermentation broth by a solvent extraction procedure using ethyl acetate and employing the following procedure:

(a) Extract the whole broth at pH 7 using two volumes of solvent each time for each volume of broth;

(b) Combine the solvent extracts and remove the ethyl acetate by stripping to yield a solid residue;

(c) Dissolve the residue in acetone;

(d) Add a mixture of 6:4 (v/v) ethyl ether:hexane until a precipitate forms;

(e) Filter the resulting precipitate and dry the precipitate in a vacuum.

Using the above procedure, 4 gm of antibiotic 13-384 complex were obtained from 60 liters of broth.

Antibiotic 13-384 complex was characterized by paper and thin layer chromatography in numerous solvent systems. Table 1 lists the Rf values of the complex in some of the solvent systems employed.

TABLE 1

Chromatography of Antibiotic 13-384 Complex

| | Rf |
|---|---|
| Paper Chromatography System | |
| n-butanol:water:acetic acid (v/v) (4:5:1) upper phase used ascending | 0.93 |
| Propanol:water:acetic acid (v/v) (10:8:1) ascending | 0.96 |
| Propanol:pyridine:acetic acid:water (v/v) (15:10:3:12) ascending | 1.00 |
| 80% methanol plus 3% sodium chloride (w/v)* | 0.95 |
| Chloroform:Methanol:17% Ammonia (v/v) (2:1:1) | 0.60, 0.84, 1.0 |
| Thin Layer Chromatographic System | |
| Acetone:Toluene (v/v) (3:2) | 0.07, 0.22, 0.44 |
| Chloroform 100% | 0.00 |
| Chloroform:methanol (v/v) (9:1) | 0.00, 0.04 0.37, 0.48 0.56, 0.77 |
| Methanol 100% | 0.70, 0.80 |
| Toluene:methanol (v/v) (96:4) | 0.00 |
| Toluene:methanol (v/v) (94:6) | 0.00 |
| Toluene:methanol (v/v) (22:3) | 0.07, 0.18, 0.21 |

*Paper buffered with 0.95 M Na$_2$SO$_4$ plus 0.05 M NaHSO$_4$.

Since the antibiotic 13-384 complex is made up of dissimilar components, no meaningful infrared, ultraviolet, nuclear magnetic resonance or elemental analyses can be determined for the complex.

Antibiotic 13-384 components 1 and 5 were determined to be novel by infrared, hydrogen-1 and carbon-13 nuclear magnetic resonance, mass and ultraviolet spectral analysis.

SEPARATION OF THE ANTIBIOTIC COMPLEX

The antibiotic complex consists of 6 or more active components, 4 of which have been isolated and characterized. These components are designated antibiotic 13-384 component 1; antibiotic 13-384 component 3; antibiotic 13-384 component 3A; and antibiotic 13-384 component 5.

Components 1, 3 and 5 each can be isolated from the 13-384 complex by chromatography. Specifically, in employing column chromatography, silica gel can be employed as the column material and 9:1 (v/v) chloroform:methanol as the eluant.

Component 3A may be isolated from the 13-384 complex by extraction procedures.

This component was designated "3A" by its thin layer chromatography properties.

THE ANTIBIOTIC PRODUCTS

Physiochemical analysis of the isolated antibiotic 13-384 components 1 and 5 were made and are reported in Table 2 below.

TABLE 2
PHYSIOCHEMICAL PROPERTIES OF ANTIBIOTIC 13-384 COMPONENTS 1 AND 5

Figure 2:
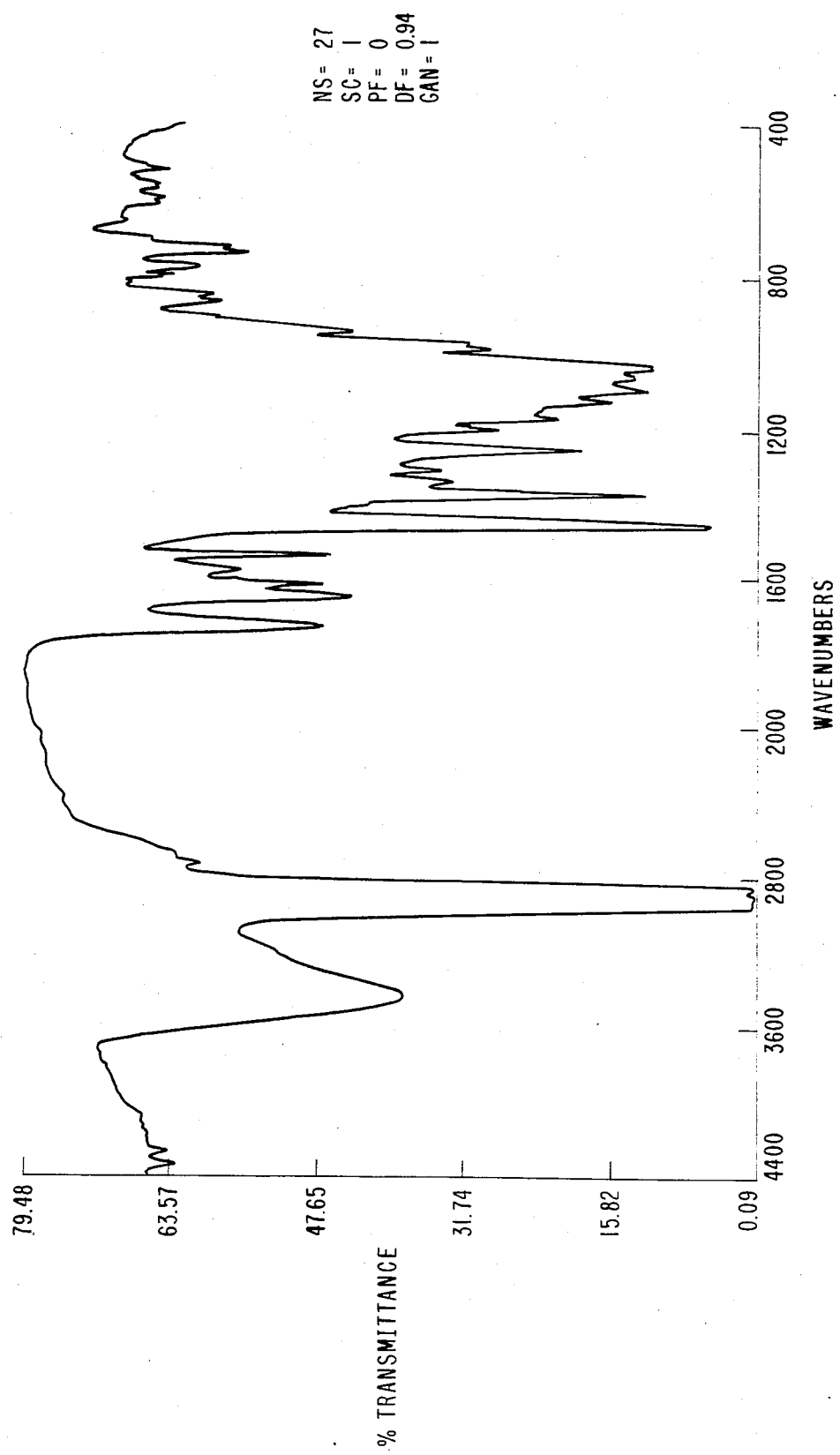
FIG. 2 is the Infrared Spectrum of Antibiotic 13-384 Component 1 in NUJOL. (A mineral-oil dispersion available from PLOUGH INC., Memphis, Tenn.).
Figure 3:
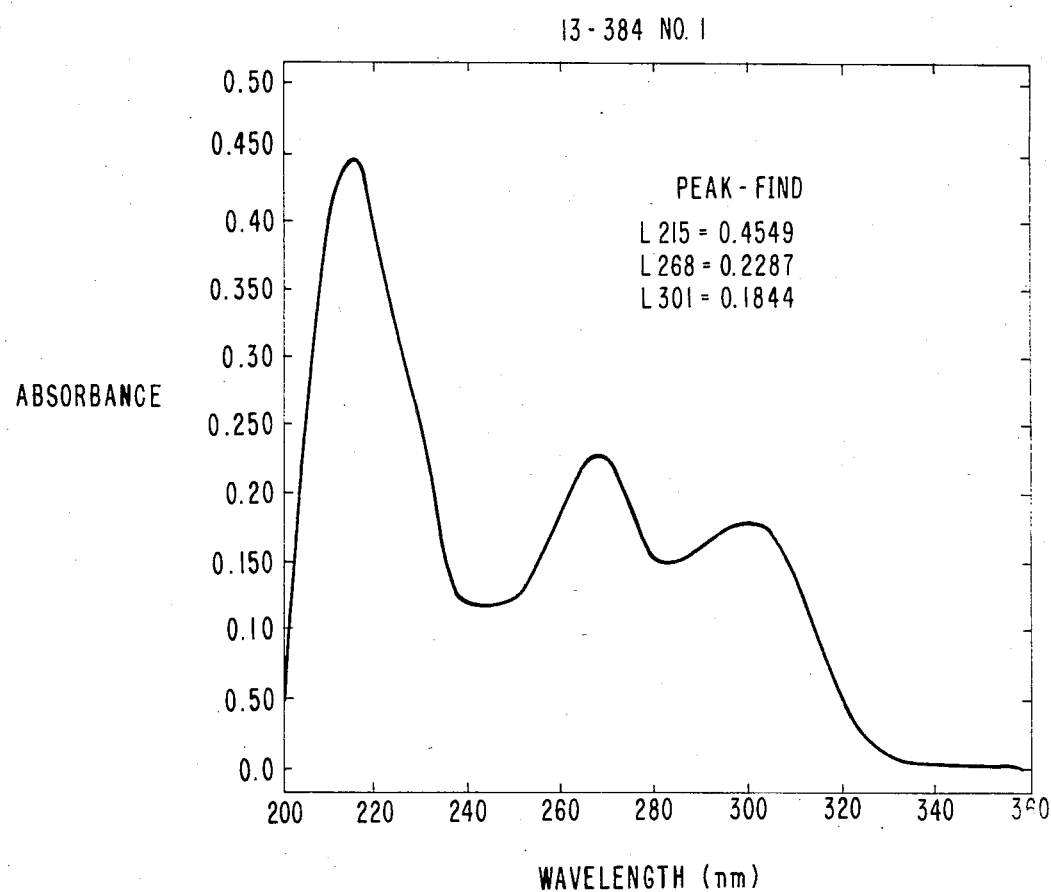
FIG. 3 is the Ultraviolet Spectrum of Antibiotic 13-384 Component 1 in methanol.
Figure 4:
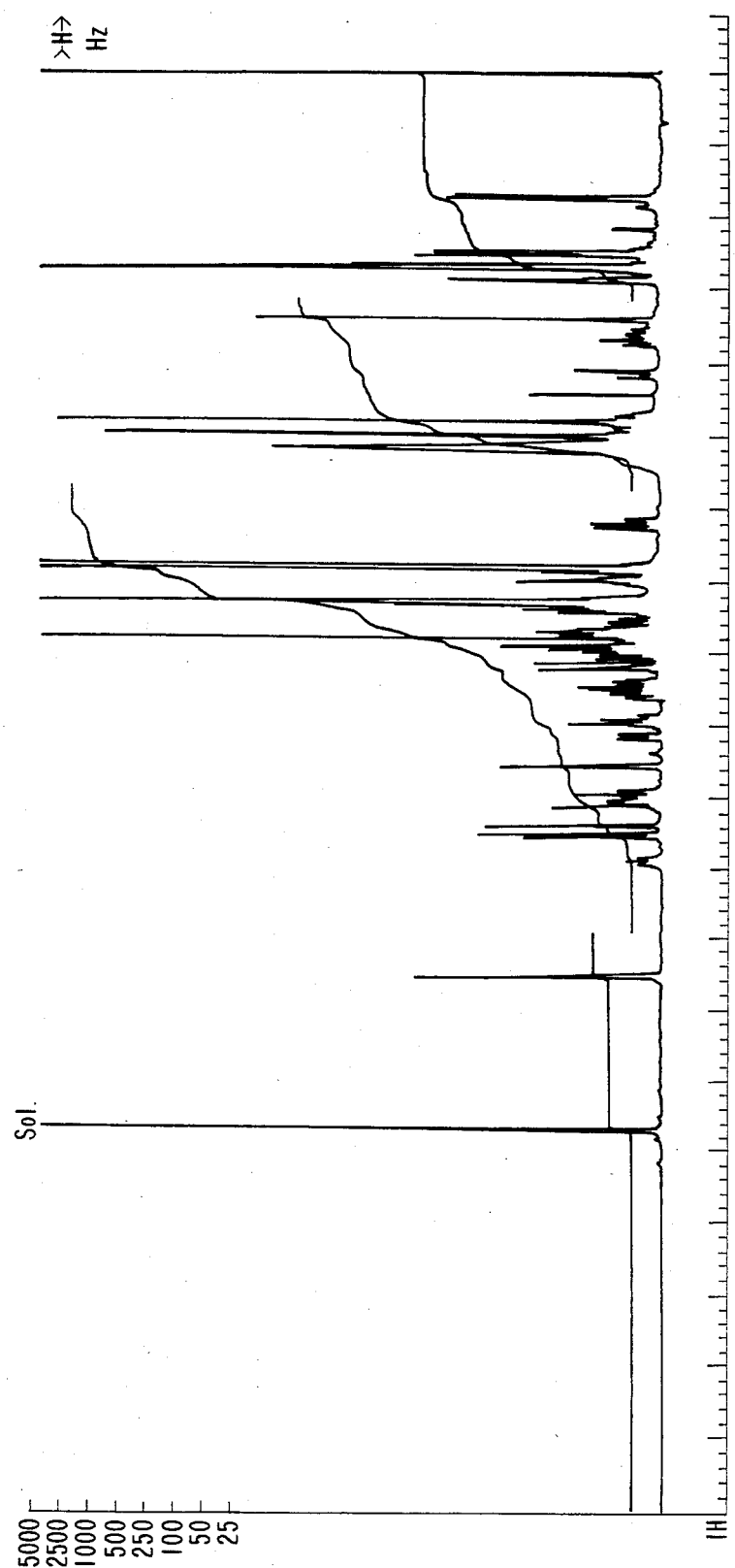
FIG. 4 is the $^1$H NMR Spectrum of Antibiotic 13-384 Component 1 in acetone-$d_6$ at 79.5 MHz.
Figure 5:
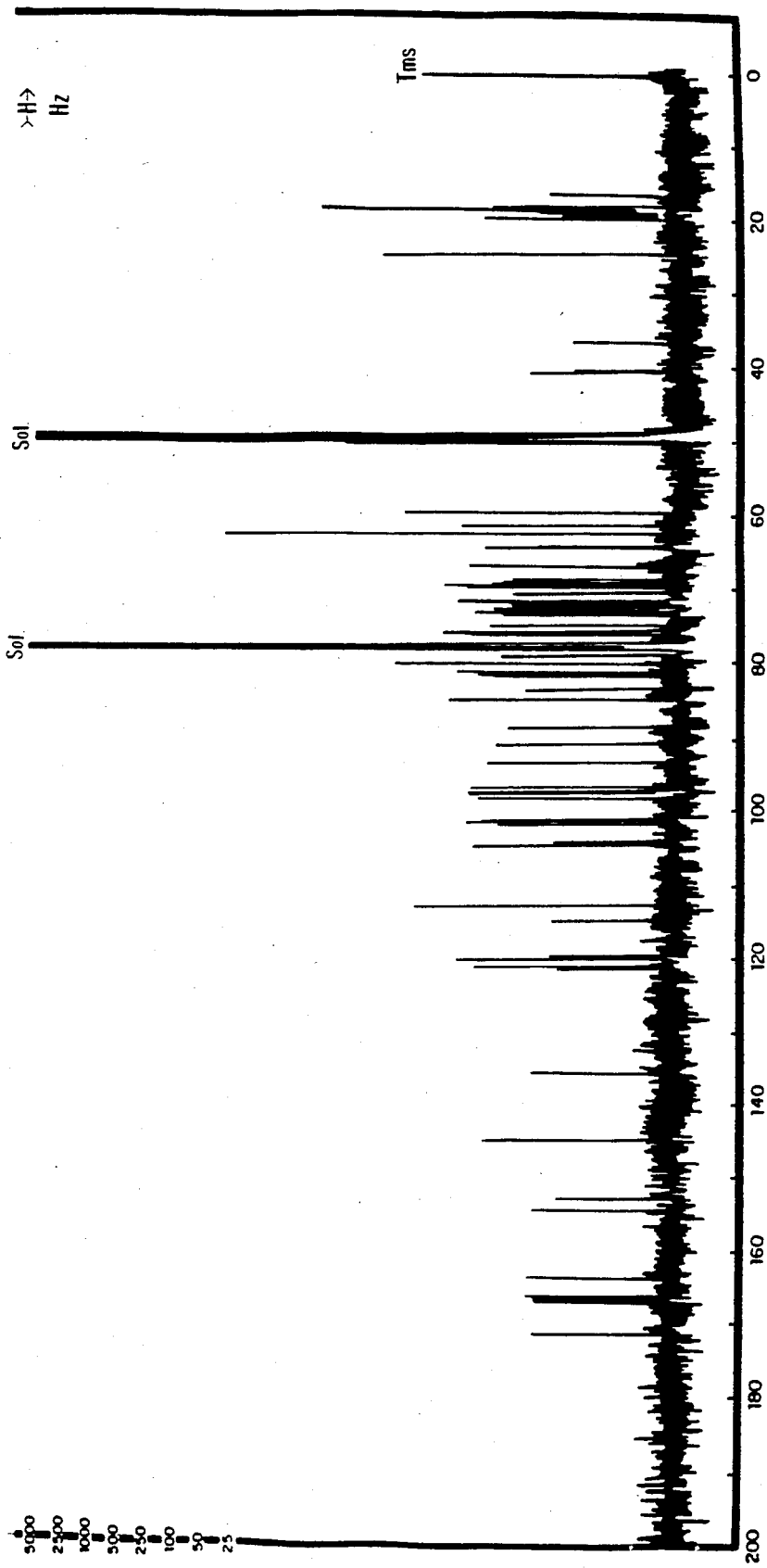
FIG. 5 is the $^{13}$C NMR Spectrum of Antibiotic 13-384 Component 1 in CDCl$_3$/CD$_3$OD at 25.2 MHz.
Figure 6:
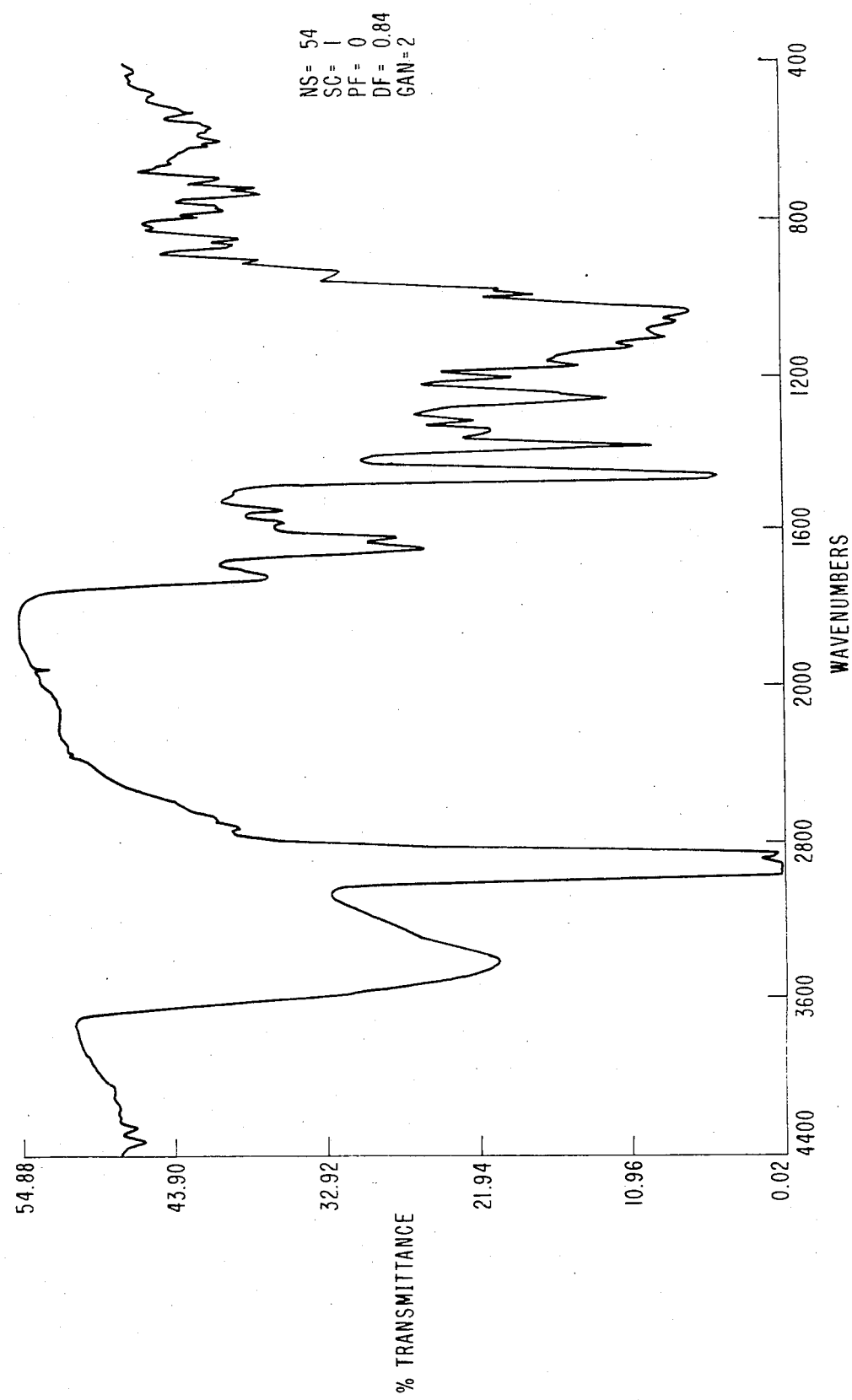
FIG. 6 is the Infrared Spectrum of Antibiotic 13-384 Component 5 in NUJOL.
Figure 7:
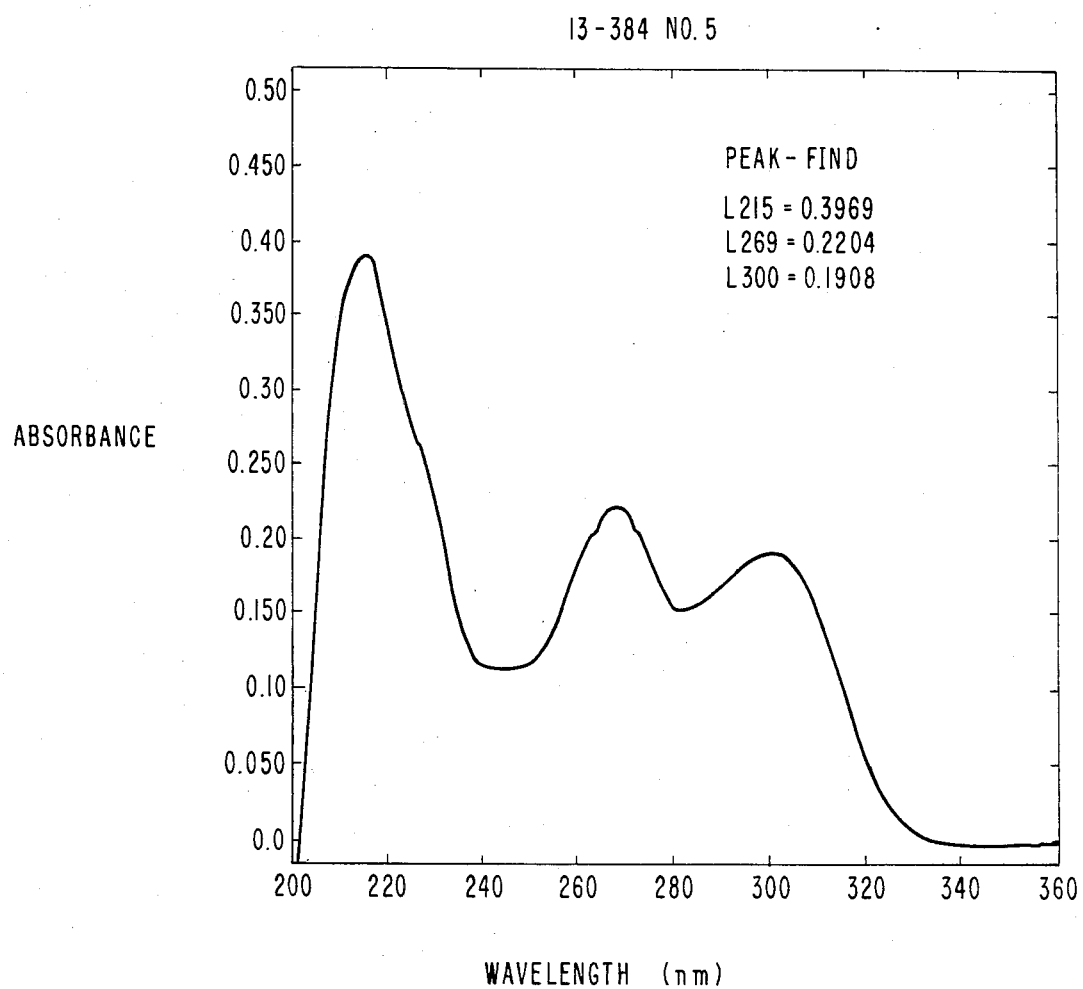
FIG. 7 is the Ultraviolet Spectrum of Antibiotic 13-384 Component 5 in methanol.
Figure 8:
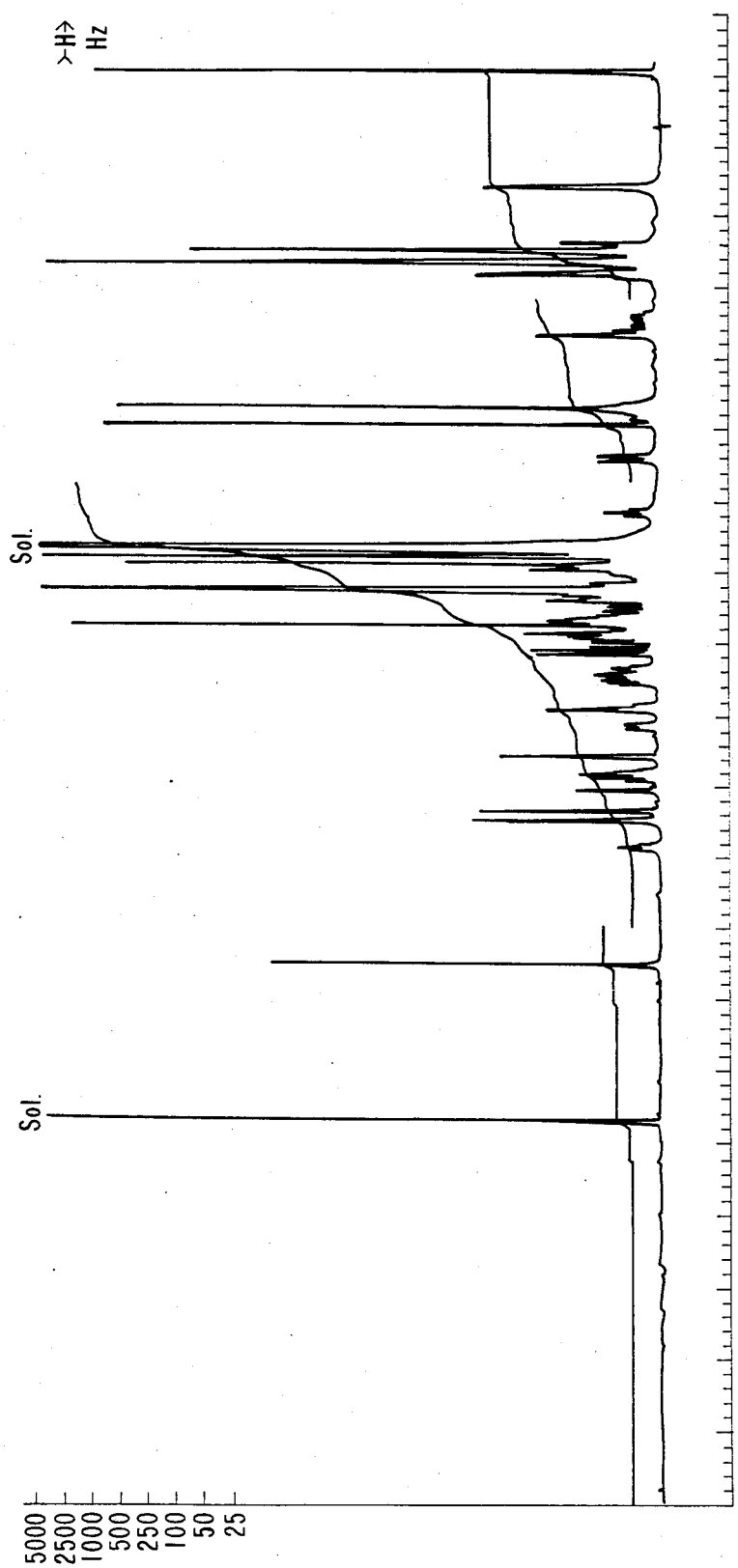
FIG. 8 is the $^1$H NMR Spectrum of Antibiotic 13-384 Component 5 in acetone-$d_6$ at 79.5 MHz.
Figure 9:
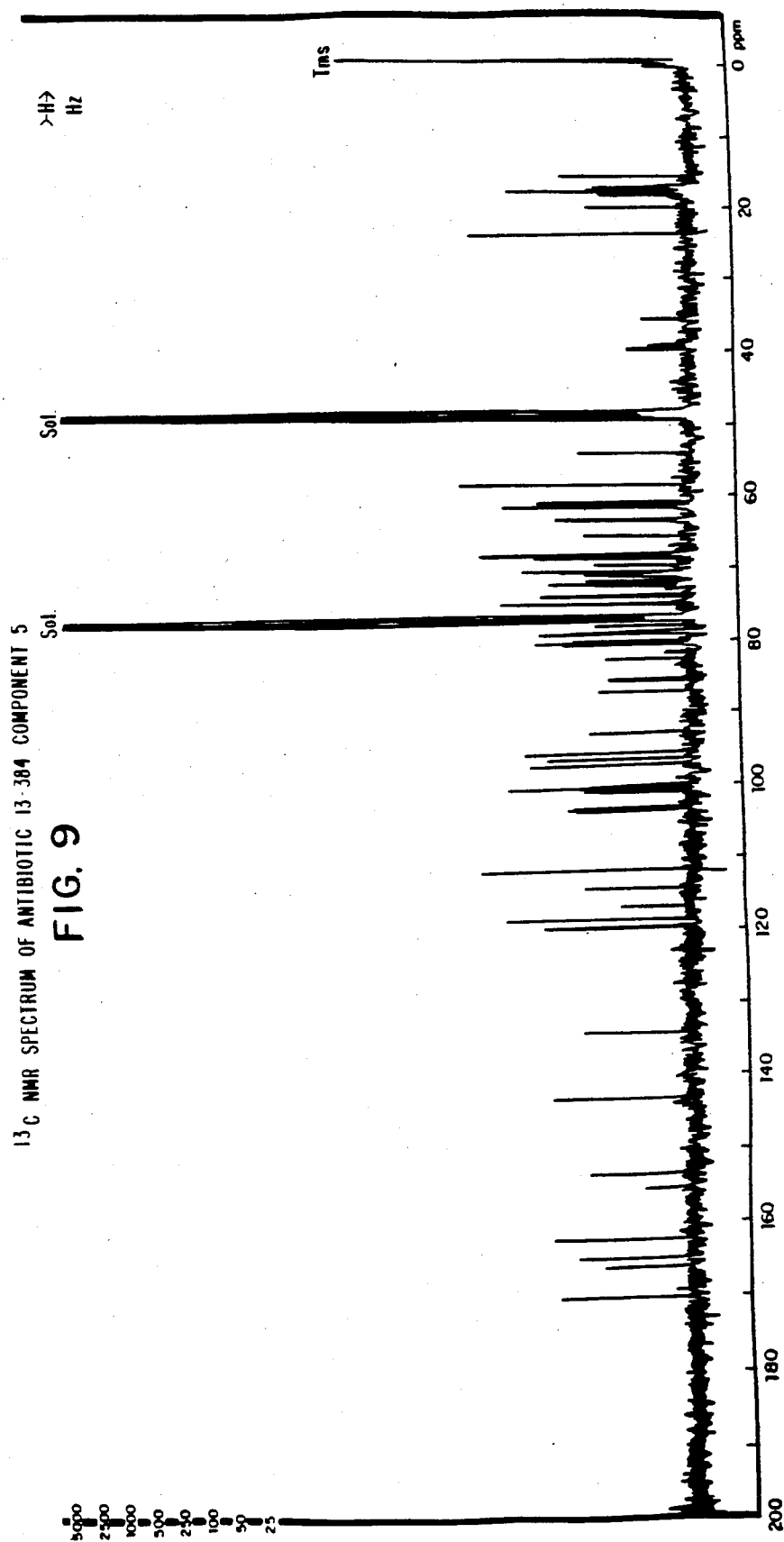
FIG. 9 is the $^{13}$C NMR Spectrum of Antibiotic 13-384 Component 5 in CDCl$_3$/CD$_3$OD at 25.2 MHz.
Figure 10:
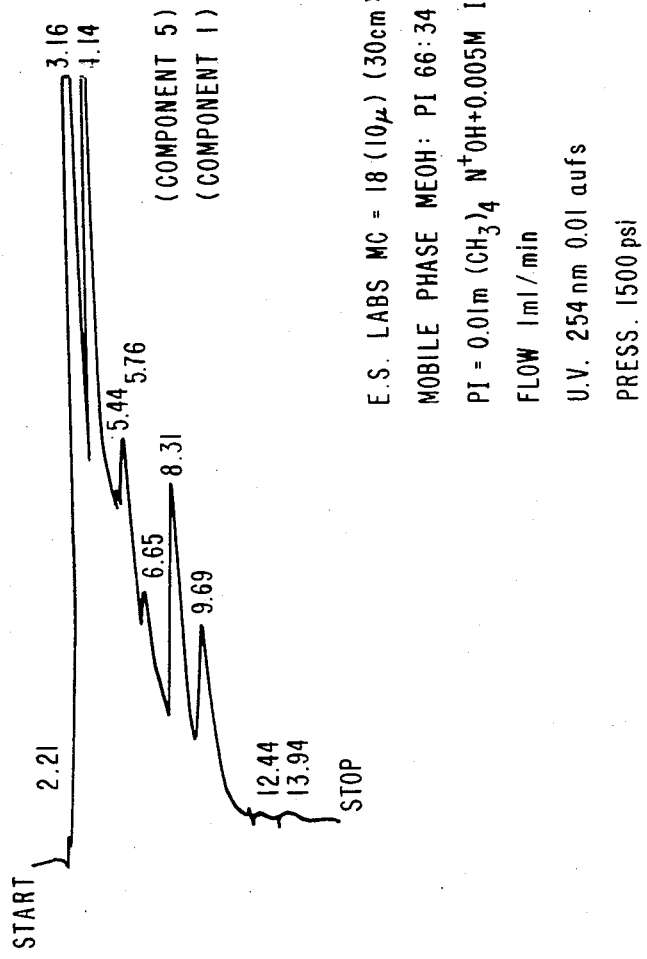
FIG. 10 is the HPLC* (HIGH PERFORMANCE LIQUID CHROMATOGRAPHY) chromatograph showing separation of components 1 and 5 of the antibiotic 13-384 complex.

|  | 1 | 5 |
|---|---|---|
| UV | FIG. 3: | FIG. 7: |
| MAX | 215 nm | 215 nm |
|  | 268 nm | 269 nm |
|  | 301 nm | 300 nm |
| $[\alpha]_D 26$ | $-42.8°$(C 0.3%, methanol) | $-42.3°$(C 0.3%, methanol) |
| Molecular[a] Elemental Analysis: | $C_{70}H_{97}O_{38}NCl_2$ | $C_{70}H_{99}O_{36}NCl_2$ |
| C | 50.96 | 48.66[b] |
| H | 6.00 | 5.98[b] |
| N | 0.72 | 1.20[b] |
| Cl | 4.8 | 3.91 |
| Molecular Weight[c] | 1629 | 1599 |
| IR Absoption | FIG. 2 | FIG. 6 |
| $_{13}$C NMR | FIG. 5 | FIG. 9 |
|  | 120.4 ppm | 120.4 ppm |
|  | 119.3 ppm | 119.3 ppm |
| $_1$H NMR | FIG. 4 | FIG. 8 |

[a]Determined by analysis of high resolvtion Fast Atom Bombardment mass spectral data.
[b]Average of two analyses
[c]Determined by Fast Atom Bombardment mass spectrum.

Components 1 and 5 were further characterized by infrared (IR) and ultraviolet (UV) and proton and carbon-13 nuclear magnetic resonance ($^1$H and $^{13}$C nmr) spectral analysis and by Fast Atom Bombardment mass spectrometry (FAB-MS). From the above spectral analysis, it was determined that components 1 and 5 of antibiotic complex 13-384 were novel. Components 1 and 5 were characterized as novel everninomicins in the $^1$H NMR by the benzoate hydrogen resonances at δ:6.26 ppm. Components 1 and 5 were examined by C-13 nuclear magnetic spectroscopy. Evaluation of the C-13 data showed the presence of two ortho ester type carbons around 119.3 ppm and 120.4 ppm for component 1 of antibiotic 13-384, and around 119.3 ppm and 120.4 ppm for component 5; such resonances are characteristic of members of the everninomicin class of antibiotics.

Component 3A was determined by IR, UV, $^1$H and $^{13}$C NMR and mass spectral anaylsis to be chloramphenicol.

Component 3 was examined by spectral analysis and determined to be structurally related to thiostrepton, a polypeptide antibiotic containing sulfur.

BIOLOGICAL PROPERTIES OF ANTIBIOTIC 13-384 COMPONENTS 1 AND 5

Antibiotic 13-384 components 1 and 5 were tested both in-vitro and in-vivo to determine antibacterial acitivty against a variety of gram-positive and gram-negative organisms.

In-vitro antibacterial activity tests were performed via conventional agar dilution methods in Mueller-Hinton agar(MHA).

Antibiotic 13-384 component 1 was determined to be active against gram-positive bacteria. Greatest antibacterial in-vitro activity was against Staphylococci with a mean Minimum Inhibitory Concentration (MIC) of 0.03 (mcg/mL, MHA, 24 hrs.) for 22 strains of Staphylococci with MIC's of individual strains ranging from 0.016 for Staphylococcus strain Ziegler to 0.125 for Staphylococcus strain 76070108.

Antibiotic 13-384 component 5 was determined to be active against both gram-negative and gram-positive bacteria as shown by in-vitro activity against a variety of gram-negative and gram-positive bacteria. Minimum Inhibitory Concentration (MIC) ranged from 2(mcg/mL MHA, 24 hrs.) for *Escherichia coli* ATCC 10536 to 128 for Serratia 0630702 with a geometric mean MIC of 100.4 for all 57 grams negative bacteria. Gram-positive activity was determined using various strains of Staphylococci. Component 5 had a geometric mean Minimum Inhibitory Concentration of 2.2 (mcg/mL, MHA, 24 hrs) against 11 strains of Staphylococci with MIC's of individual strains ranging from 2.0 for *Staphylococcus* Ziegler to 8.0 for *Staphylococcus* Grax.

In-vivo antibacterial activity of antibiotic 13-384 components 1 and 5 were determined in mice via subcutaneous administration.

Antibiotic 13-384 components 1 and 5 were determined to exhibit subcutaneous protective activity against *S. aureus* and *E. coli* infections in mice.

Subcutaneous protective activity is expressed in terms of a PD$_{50}$ (Protective Dosage). PD$_{50}$ values for a variety of organisms are reported in 50 Table 3.

TABLE 3
In Vivo Subcutaneous Activity of Antibiotic 13-384 Components 1 and 5 Against Bacterial Infections in Mice

|  | Exp. No. | Organism | PD$_{50}$ (mg/kg 72 hrs.) |
|---|---|---|---|
| component 5 Na Salt | 1 | E. coli-Jordan | 4.5 |
| component 5 Na Salt |  | S. aureus-Giorgio | 3.0 |
| component 1 Na Salt |  | E. coli-Jordan | 13.0 |
| component 1 Na Salt |  | S. aureus-Giorgio | 6.5 |
| component 5 | 2 | E. coli-Jordan | 45 |
| component 5 |  | S. aureus-Giorgio | 12.5 |
| component 1 |  | E. coli-Jordan | 55 |
| component 1 |  | S. aureus-Giorgio | 65 |
| component 1 | 3 | E. coli-Jordan | 50 |
| component 5 |  | E. coli-Jordan | 40 |
| component 5 | 4 | E. coli-1574-1 | 100 |
| component 5 |  | S. aureus-Giorgio | 55 |
| Intravenous Acute Toxicity | | | |
| Component 1 |  | LD$_{50}$ | 320 mg/kg |
| Component 5 |  | LD$_{50}$ | 140 mg/kg |

Antibiotic 13-384 complex and components 1 and 5 thereof are active against bacteria.

The present invention contemplates a method of eliciting an antibacterial effect in a mammal having a susceptible bacterial infection which comprises administering to said mammal a therapeutically effective quantity of a composition of matter selected from the group consisting of antibiotic 13-384 complex, antibiotic 13-384 component 1, and antibiotic 13-384 component 5.

The methods of this invention are implemented using pharmaceutical compositions comprising a pharmaceutically acceptable carrier and a therapeutically effective quantity of a composition of matter selected from the group consisting of antibiotic 13-384 complex, antibiotic 13-384 component 1, and antibiotic 13-384 component 5.

As such, the antibiotics may be combined with any suitable pharmaceutical carrier and administered orally, parenterally or topically in a variety of formulations. For oral administration, the antibiotics of this invention may be compounded in the form of tablets, capsules, elixirs or the like. Tablets and capsules may contain such excipients as starch or lactose; liquid forms may contain coloring or flavoring agents. Topical preparations may be in the form of creams, hydrophobic and hydrophylic ointments, or aqueous, non-aqueous or emulsion-type lotions. Typical carriers for such formulations are water, oils, greases, polyesters and polyols. Parenteral formulations, e.g., injectible dosage forms, are usually liquids such as solutions or suspensions, with typical carriers being distilled water and saline solution.

The dose to be administered in any particular dosage form will depend upon various factors, such as the characteristics of the animal species being treated, the susceptibility of the infecting organism to the antibiotic, the stage and severity of the infection. Generally, the dosage administered is from about 1.0 mg to about 25 mg per kilogram of body weight per day, in divided dosages, the specified dosage being left to the discretion of the practitioner.

In treating certain patients with the compounds of this invention, it is possible to include other pharmaceutically active ingredients in the same dosage unit.

The Microorganism

The microorganism used, according to this invention, for the production of antibiotic 13-384 complex is *Micromonospora carbonacea* var *africana* var nov.

A culture of this microorganism has been deposited with the Northern Utilization and Research Division, Agriculture Research Service, U.S. Department of Agriculture in Peoria, Ill. where it has been assigned accession number NRRL 15099. Subcultures of *Micromonospora carbonacea* var *africana* NRRL 15099 are available to the public without restriction from the aforementioned agency. A culture of this microorganism has been made a part of the collection of the American Type Culture Collection (ATCC) in Rockville, Md. where it has been assigned accession number ATCC 39149. Subcultures of *Micromonospora carbonacea* var *africana* ATCC 39149 are available to the public without restriction. Use of the microorganism is dependent on U.S. Patent Laws.

The microorganism was isolated from a sample of mud obtained from the bank of the Nyiro River in Kenya, Africa. It has been characterized and found to have the microscopic, macroscopic, and whole cell hydrolysis properties of the genus Micromonospora. See Table 4.

Based on the formation of orange vegetative mycelial pigments, red to orange diffusable pigments (Table 5) and carbohydrate utilization and physiologic characteristics such as good growth on mannitol, rhammose and in the presence of aminoglycoside antibiotics (Tables 6 and 7, respectively), this culture is most closely related to the described varieties of *Micromonospora carbonacea* [Luedemann, G. M., and B. Brodsky, 1965, pg. 47–52, Antimicrob Agents Chemother, (1964)].

The microorganism may be distinguished from these varieties by several taxonomical parameters. For example, it can be distinguished from *Micromonospora carbonacea* var *carbonacea* ATCC 27114 by sporulation patterns, diffusible pigment formation, ability to form nitrite from nitrate and antibiotic production and from *Micromonospora carbonacea* var *aurantraca* ATCC 27115 in antibiotic production.

On the basis of these distinctions the new culture is considered to be a new variety of the species *Micromonospora carbonacea*. It is proposed that the culture be designated *Micromonospora carbonacea* var *africana* NRRL 15099, ATCC 39149. This strain is under stood to be the type strain of the new variety.

The taxonomic methods used herein were those cited in Luedemann and Brodsky, Antimicrob Agents Chemotherapy, pp 47–52, "*Micromonospora carbonacea* sp. n., an eveininomicin-producing organism", 1964; Horan and Brodsky, International Journal Syst. Bacterial., Vol. 32, ppg 195–200, "A Novel Antibiotic-Producing *Actinomadura, actinonadura kijaniata* sp. nov.", 1982; Becker et al, Applied Microbiology, Vol. 13, ppg 236–243, "Chemical Composition of Cell Wall Preparations from Strains of Various Genera of Aerobic Actinomycetes", 1966; Lechevalier and Lechevalier, International Journal Syst. Bacterial. Vol. 20, ppg 487–493, "Chemical Composition as a Criterion in the Classification of Aerobic Actinomycetes, 1970; Shirling and Gottlieb, International Journal Syst. Bacteriol, Vol. 16, ppg 313–340, "Methods for Characterization of Streptomyces Species, 1966; and Waksman, *The Actinomycetes* Vol. 2., (The Williams & Wilkins Co., Baltimore, Md., 1961).

In the description of the *Micromonspora carbonacea* var *africana* NRRL 15099 in Table 5, two color designators are employed. The first is a color name taken from the "Descriptive Color Name Dictionary" by Taylor, Knoche and Granville published by the Container Corporation of America (1950) U.S.A., with a color chip number corresponding to the color name, the chip number being taken from "The Color Harmony Manual,: 4th Edition, 1958, also published by the Container Corporation of America. The second designator consists of a color name and number which refers to the synonym and near synonym found in the National Bureau of Standards, Circular 553, Nov. 1, 1965 (U.S.A.).

TABLE 4

Characteristics of *Micromonospora Carbonacea* var *Africana* NRRL 15099

| Organism | Macroscopic | Microscopic |
|---|---|---|
| | Aerial Mycelium not formed | |
| *Micromonospora carbonacea* var *africana* | Vegetative mycelial pigmentation ranges from light to bright orange. The culture grows well on most rich organic media after producing bright orange to red diffusable pigments. Poor growth to no growth occurs on glycerol-asparagine and peptone-iron agars. Melanin and hydrogen | The culture rarely formes spores; when present the spores usually occur singly, usually sessile and appear along the length of fine, 0.5 to 0.8 micron slightly branched vegetative mycelia; spores have irregular outline and measure 1 to 1.2 microns in |

TABLE 4-continued
Characteristics of *Micromonospora Carbonacea* var *Africana* NRRL 15099

| Organism | Macroscopic | Microscopic |
|---|---|---|
| | sulfide are not formed. | diameter. |

Culture characteristics of the microorganism, *Micromonospora carbonacea* var *africana* NRRL 15099, ATCC 39149 on various standard media are reported in Table 5.

Growth of the microorganism, NRRL 15099/ATCC 39149 on various carbon compounds is reported in Table 6.

Physiologic characteristics of microorganism, NRRL 15099/ATCC 39149 are reported in Table 7.

Whole cell analysis of the culture of the microorganism NRRL 15099/ATCC 39149 found mesodiaminopimelic acid, xylose and arabinose.

Growth of the culture is found from 27° to 40° C. on yeast-dextrose agar. Poor growth is found at 45° C. with optimum growth at from 27° to 35° C.

TABLE 5
Growth Characteristics of *Micromonospora Carbonacea* var *africana* NRRL 15099 on Various Descriptive Media[1]

| Medium | Growth Characteristics |
|---|---|
| Bennett's Agar | G: +++, good |
| | S: Raised, plicate |
| | AM: Absent |
| | DFP: Present, yellow-orange |
| | C: g 5 na, bright orange |
| Czapek Sucrose Agar | G: ++, moderate |
| | S: Slightly raised, folded, hard |
| | AM: Absent |
| | DFP: Present, yellow-orange |
| | C: g 5 nc, burnt orange |
| Glucose-Asparagine Agar | G: +, fair |
| | S: Slightly raised, folded |
| | AM: Absent |
| | DFP: Present, yellow-orange |
| | C: g 4 la, orange |
| Glycerol-Asparagine Agar (ISP #5) | G: ±, poor |
| | S: |
| | AM: Non-characteristic |
| | DFP: |
| | C: |
| Nutrient Agar | G: ± to +, poor to fair |
| | S: Flat, granular |
| | AM: Absent |
| | DFP: Absent |
| | C: g 3 ec, bisque |
| Peptone Glucose Agar | G: ±, poor |
| | S: |
| | AM: Non-characteristic |
| | DFP: |
| | C: |
| Potato Dextrose Agar | G: ±, poor to fair |
| | S: Flat, granular |
| | AM: Absent |
| | DFP: Absent |
| | C: g 3 ec, bisque |
| Emerson's Agar | G: + to ++, fair to moderate |
| | S: Flat, granular |
| | AM: Absent |
| | DFP: Present, yellow-orange |
| | C: g 4 ia, apricot |
| N-Z Amine Type A Agar | G: +++, good |
| | S: Raised, deeply folded |
| | AM: Absent |
| | DFP: Absent |
| | C: g 5 nc, burnt orange |
| Yeast Extract Glucose Agar | G: +++, good |
| | S: Raised, soft, folded |
| | AM: Absent |
| | DFP: Present, faint red brown |
| | C: g 4 ia, apricot |

TABLE 5-continued
Growth Characteristics of *Micromonospora Carbonacea* var *africana* NRRL 15099 on Various Descriptive Media[1]

| Medium | Growth Characteristics |
|---|---|
| | g p, black specs |
| Tomato Paste-Oatmeal Agar | G: +++, good |
| | S: Raised, granular to folded, ribbon like |
| | AM: Absent |
| | DFP: Present, red-orange |
| | C: g 5 na, bright orange |
| Water Agar | G: ±, poor |
| | S: |
| | AM: Non-characteristic |
| | DFP: |
| | C: |
| Yeast Extract Malt Extract Agar (ISP #2) | G: +++, good |
| | S: Raised, deeply folded, waxy |
| | AM: Absent |
| | DFP: Present, red-orange |
| | C: g 5 na, bright orange |
| Oatmeal Agar (ISP #3) | G: +, fair |
| | S: Flat, granular |
| | AM: Absent |
| | DFP: Present, red-orange |
| | C: g 4 la, orange |
| Inorganic Salts-Starch Agar (ISP #4) | G: + to ++, fair to moderate |
| | S: Flat, granular |
| | AM: Absent |
| | DFP: Present, yellow-orange |
| | C: g 5 nc, burnt orange |
| Starch Agar (Waksman #21) | G: +, fair |
| | S: Flat, granular |
| | AM: Absent |
| | DFP: Present, yellow-orange |
| | C: g 4 nc, russet orange |
| Calcium Maleate Agar | G: +, fair to poor |
| | S: Flat, granular |
| | AM: Absent |
| | DFP: Present, faint yellow-orange |
| | C: g 4 la, orange |
| Tyrosine Agar (ISP #7) | G: +, fair to poor |
| | S: Flat, granular |
| | AM: Absent |
| | DFP: Absent |
| | C: g 4 le, maple |
| Starch Agar (Gordon) | G: +++, good |
| | S: Raised, deeply folded, waxy |
| | AM: Absent |
| | DFP: Present, red-orange |
| | C: g 5 la, sun orange |
| Casein Agar (Gordon) | G: ++, moderate |
| | S: Slightly raised, granular |
| | AM: Absent |
| | DFP: Absent |
| | C: g 4 ie, cork tan |
| Gelatin Agar (McDade) | G: +, fair |
| | S: Flat, granular |
| | AM: Absent |
| | DFP: Absent |
| | C: g 3 ie, camel |

Footnotes to Table 5
[1]Observations made after 14-21 days at 30° C.
G, growth; S, surface; AM, aerial mycelium; DFP, diffusable pigment; C, color.

TABLE 6
Carbohydrate Utilization[1] of *Micromonospora carbonacea* Var *africana* NRRL 15099

| Utilization of: | Result |
|---|---|
| D-Arabinose | −, poor |
| L-Arabinose | +++, good* |
| Cellibiose | +++, good* |
| Dulcitol | −, poor |
| Erythritol | −, poor |
| Fructose | ++, good |
| L-Fucose | −, poor |
| Galactose | +++, good* |
| Glucose- | +++, good* |
| m-d-glucoside | −, poor |

TABLE 6-continued

Carbohydrate Utilization[1] of *Micromonospora carbonacea* Var *africana* NRRL 15099

| Utilization of: | Result |
|---|---|
| Inositol | −, poor |
| Inulin | ++, moderate |
| Lactose | ++, moderate |
| Maltose | +++, good* |
| Mannitol | −, poor |
| Mannose | +++, good |
| Melibiose | +++, good* |
| Raffinose | −, poor |
| Rhamnose | −, poor |
| Ribose | −, poor |
| Sucrose | +++, good* |
| Trehalose | +++, good |
| D-xylose | +++, good* |

*Yellow diffusable pigment
[1]Medium of Luedemann and Brodsky (Antimicrob. Ag. Chemoth., 1965)

TABLE 7

PHYSIOLOGIC CHARACTERISTICS OF *MICROMONOSPORA CARBONACEA* VAR *AFRICANA* NRRL 15099

| Test | Result |
|---|---|
| Utilization of: | |
| Acetate | + |
| Benzoate | − |
| Butyrate | + |
| Glucuronate | − |
| Glutamate | + |
| Propionate | + |
| Pyruvate | + |
| Tartrate | − |
| Growth in the presence of: | |
| Antibiotics at 50 mcg/mL | |
| Gentamicin | − |
| Sisomicin | − |
| Neomycin | − |
| Kanamycin | − |
| Erythromycin | − |
| Rosaramicin | + |
| Lincomycin | + |
| Clindamycin | + |
| Everninomicin | + |
| NaCl | |
| 1.0% | ++, moderate |
| 2.0% | ±, poor |
| 3.0% | ±, poor |
| $Na_2S_2O_3$ | |
| 1.0% | ++, moderate |
| 2.0% | ±, poor |
| 3.0% | ±, poor |
| Hydrolysis of: | |
| Adenine | +, weak |
| Hypoxanthine | − |
| Tyrosine | + |
| Xanthine | − |
| Chitin | + |
| Casein | + |
| Starch | + |
| DNA | + |
| Gelatin | + |
| Xylan | + |
| Breakdown of: | |
| Urea | + |
| Allantoin | − |
| Nitrate to nitrite: | − |
| Growth at: | |
| 27° C. | +++, good |
| 35° C. | +++, good |
| 40° C. | ++, moderate |
| 45° C. | −, poor |
| 50° C./8 hr. | ++, moderate |

FERMENTATION OF THE MICROORGANISM

Antibiotic 13-384 complex is produced when the elaborating microorganism, *Micromonospora carbonacea* var *africana*, is grown in an aqueous nutrient medium under submerged aerobic conditions at a temperature of about 27° C. to 40° C., preferably at from 27° C. to 35° C., and at a pH of from about 6.5 to 8.0 with agitation until substantial antibiotic activity is imparted to the medium. Temperature studies indicate that the organism grows much more rapidly at 34° C. then at 30° C. However, antibiotic production is greater if the temperature is lowered to 30° C. at the end of the exponential growth period. Therefore, the fermentation is preferably conducted employing a two temperature pattern of 34° C. for the first 24 hours and 30° C. for the period 24 to 96 hours. The rate of growth for the organism at several temperatures is shown in Table 7. The fermentation is generally conducted from 3 to 7 days although preferably for 4 days. To determine when peak antibiotic production has been reached, samples of the medium were assayed every 24 hours for antibiotic content by bioassay of the whole broth against *S. aureus* ATCC 6538P (pH 7.0) and *E. coli* ATCC 10536 (pH 8.0). The growth of the organism (packed cell volume), pH and dissolved oxygen levels were determined either intermittantly or continuously and are shown in FIG. 1.

As nutrient medium, there is employed any suitable medium containing a source of carbon, for example an assimilable carbohydrate, and a source of nitrogen, for example an assimilable nitrogenous or proteinaceous material.

The medium initially employed for the fermentation contained NZ-Amine A (an enzymatic hydrolysate of casein) and soluble starch as the major sources of nitrogen and carbon. Under these conditions, the microorganism produced 6 components in the antibiotic complex; component 1, component 2, component 3, component 4, component 5 and component 6 as determined by bioautography of the complex after development of a thin layer chromatography plate in 9:1 (v/v) chloroform:methanol.

Replacement of casein hydrolysate by either meat or fish peptone and substituting potato dextrin for soluble starch enhanced the total antibiotic production as revealed by a significant increase in activity against *E. coli*. Bioautography of the antibiotic complex revealed significant increases in components 1 and 5 and in addition the presence of a new component designated component 3A.

Tables 8A and 8B lists several media useful for the production of antibiotic 13-384. Media B, C and D are especially suited for antibiotic production. The addition of magnesium sulfate and dipotassium phosphate in media C and D produced clearer zones of inhibition in bioassays against *E. coli*. In batch fermentations for production of bulk material, medium B is preferred.

TABLE 8

FERMENTATION GROWTH MEDIUM

| INGREDIENT | MEDIUM A* | MEDIUM B** |
|---|---|---|
| Yeast Extract | 0.5% | 5 g |
| Fish Peptone | — | 6 g |
| A.M.P. - R.S.5) | | |
| Meat Peptone | — | — |
| (Hormel Super-Dried | | |
| Meat Solubles) | | |
| Cerelose | 1.0% | 20 g |

TABLE 8-continued

| FERMENTATION GROWTH MEDIUM | | |
|---|---|---|
| INGREDIENT | | |
| Potato Dextrin | — | 40 g |
| Calcium Carbonate | 0.4% | 4 g |
| Cobalt Chloride | 0.024 mg % | $1 \times 10^{-6}$ M |
| K$_2$HPO$_4$ | — | — |
| MgSO$_4$.7H$_2$O | — | — |
| Casein Hydrolysate | 0.5% | — |
| Soluble Starch | 2.0% | — |
| | MEDIUM C** | MEDIUM D** |
| Yeast Extract | 5 g | 5 g |
| Fish Peptone (A.M.P. - R.S.5) | 6 g | — |
| Meat Peptone (Hormel Super-Dried Meat Solubles) | — | 6 g |
| Cerelose | 20 g | 20 g |
| Potato Dextrin | 40 g | 40 g |
| Calcium Carbonate | 4 g | 4 g |
| Cobalt Chloride | $1 \times 10^{-6}$ M | $1 \times 10^{-6}$ M |
| K$_2$HPO$_4$ | 0.75 g | 0.75 g |
| MgSO$_4$.7H$_2$O | 2.0 g | 2.0 g |
| Casein Hydrolysate | — | — |
| Soluble Starch | — | — |

*percent by weight
**grams/liter

The foregoing media are exemplary of the nutrients utilized by *Micromonospora carbonacea* var *africana* to produce antibiotic 13-384 complex. However, it is obvious to those skilled in the fermentation art that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 6.7 and prior to inoculation the pH is usually adjusted to 7.0.

The fermentation was initiated by addition of the inoculum (generally 2.5% of inoculum by volume of total broth) to the broth. The inoculum was prepared by addition of a sample of the frozen whole broth to an appropriate medium. A particularly preferred medium comprises beef extract, 0.3%; tryptose, 0.5%; dextrose, 0.1%; potato starch, 2.4%; yeast extract, 0.5%; and calcium carbonate, 0.2%. The pH of the inoculum medium is adjusted to 7.5 prior to sterilization. The inoculum stage of the fermentation usually requires from 24 to 120 hours with 1 to 2 days preferred and is generally conducted at about 30° C.

EXAMPLE 1

Preparation of Antibiotic 13-384 Complex

A. Inoculum Preparation
Prepare a 250 ml Erlenmeyer flask with 50 mL of the following germination medium:
Beef Extract: 3 g
Tryptose: 5 g
Yeast Extract: 5 g
Dextrose: 1 g
Starch: 24 g
Calcium Carbonate: 2 g
Tap water: 1000 mL
Adjust the pH of the germination broth to 7.5. Sterilize the broth and after cooling add 2.5 mL of a frozen whole broth sample from a previously prepared inoculum to the broth. Incubate at 30° C. with continual agitation at 250 rpm for 48 hours.

Transfer 2.5 mL of the germination broth to each of twenty 2-liter Erlenmeyer flasks, each containing 500 mL of the same germination medium and which had been previously pH adjusted and sterilized. Incubate at 30° C. with continual agitation at 250 rpm for 48 hours.

Transfer 500 ml of the second-stage germination to 14 L tanks containing 10 L of the same germination medium and which had been previously pH adjusted and sterilized. Incubate at 30° C. with continual agitation for 24 hours.

B. Fermentation
In a 14 L fermentor, add 10 L of the following medium:
Yeast Extract: 5 g
Casein Hydrolysate: 5 g
Cerelose: 10 g
Soluble Starch: 20 g
Calcium Carbonate: 4 g
Cobalt Chloride: 2.4 g
Tap water: 1000 mL Adjust the pH of the medium to 6.7 and then sterilize the medium. After sterilization, adjust the pH of the medium to 7.0 with a sterile alkaline solution. Inoculate the fermentation broth with 250 mL of the third stage inoculum preparation of Step A. Incubate the fermentation mixture at 30° C. with 0.35 VVM of air and 350 rpm agitation for about 96 hours.

C. Isolation
Extract 60 L of fermentation broth of Step B at pH 7 twice with 120 L of ethyl acetate. Combine the ethyl acetate solutions and remove the solvent by stripping to give a residue. Dissolve the residue in acetone and then add a 6:4 (v/v) mixture of ethyl ether:hexane until a precipitate results. Filter the precipitate and dry in a vacuum to give 4 gm of antibiotic 13-384 complex.

EXAMPLE 2

Separation of Antibiotic 13-384 Components 1 and 5

Dissolve 4 gm of antibiotic 13-384 complex in 40 mL of chloroform:methanol (1:1 v/v) mixture. Place the solution onto a 23" by 2.5" column containing about 500 gm of silica. Elute the column with 9:1 (v/v) chloroform:methanol at a flow rate of about 1 mL per minute and in fractions of 15 mLs each. After 240 fractions, change the eluting solvent to 6:4 (v/v) chloroform:methanol and collect 100 additional 15 mL fractions.

Monitor the column by determining activity of each fraction against *S. aureus* and *E. coli* using a disc diffusion assay. Spot the active fractions on thin layer plates and develop the plates in chloroform:methanol (9:1).

Detect the antibiotic components by observation of spot color after exposing the developed places to iodine vapors and by bioautography of a duplicate plate against *S. aureus*.

Obtain component 1 by combining fractions 4 to 12. Remove the solvent by stripping to yield a residue. Dissolve the residue in 9:1 (v/v) chloroform:methanol and then add 6:4 (v/v) ethyl ether:hexane until a precipitate forms. Filter the precipitate and dry in a vacuum to give 164 mg of antibiotic 13-384 component 1.

Obtain component 5 by combining fractions 250 to 304. Remove the solvent by stripping to yield a residue. Dissolve the residue in chloroform:methanol and then add 6:4 (v/v) ethyl ether:hexane until a precipitate forms. Filter the precipitate and dry in a vacuum to give 239 mg of antibiotic 13-384 component 5.

A sample of component 1 obtained from the silica gel column was subjected to elemental and spectroscopic analysis. The molecular weight (Fast Atom Bombardment (FAB) mass spectrometry) is 1629 amu. Qualitative elemental analysis showed presence of C, H, N and Cl. Calculated for $C_{70}H_{97}O_{38}NCl_2$ (determined from the precise molecular weight measured by high resolution FAB mass spectrometry): C, 51.53; H, 5.99; N, 0.86; Cl, 4.3; Found: C, 50.96; H, 6.00; N, 0.72; Cl, 4.8. The IR, UV, $^1H$ and $^{13}C$ NMR spectra are illustrated in FIGS. 2, 3, 4 and 5, respectively.

A sample of component 5 obtained from the silica gel column was subjected to elemental and spectroscopic analysis. The molecular weight (FAB mass spectrometry) is 1599 amu. Qualitative elemental analysis showed presence of C, H, N and Cl. Calculated for $C_{70}H_{99}O_{36}NCl_2$ (determined from the precise molecular weight measured by high resolution FAB mass spectrometry): C, 52.50; H, 6.23; N, 0.87; Cl, 4.43; Found: C, 48.66*; H, 5.98*; N, 1.20*; Cl, 3.91. (*average of two analyses). The IR, UV, $^1H$ and $^{13}C$ NMR spectra are illustrated in FIGS. 6, 7, 8 and 9, respectively.

EXAMPLE 3

Analytic Separation of Components 1 and 5

Inject 6 μL of the fermentation broth onto a HPLC column of the following parameters:
Column: E. S. Industries Chromegabond MC-18
Particle Size: 10μ
Dimensions: 300 mm×4.6 mm (1×i.d.)
Flow Rate: 1.0 mL/min
Pressure: 1500 psig
Detection: uv 254 nm, 0.01 AUFS
Injection Vol: 6 μL
Mobile Phase: Methanol-paired ion 0.01M tetramethyl ammonium hydroxide $5\times10^{-3}M$ ammonium acetate; pH adjusted to 7.4

A sample chromatogram showing the separation of components 1 and 5 is shown in FIG. 12.

EXAMPLE 4

Separation of Antibiotic 13-384 Component 3

Dissolve 10 gm of antibiotic 13-384 complex in 80 mL of chloroform:methanol (1:1 v/v) mixture. Place the solution onto a 48" by 3" column containing about 1500 gm of silica gel. Elute the column with chloroform:methanol (9:1, v/v) at a flow rate of about 1 mL per minute and in fractions of 15 mL each.

Monitor the column by determining activity of each fraction against *S. aureus* and *E. coli* using a disc diffusion assay. Spot the active fractions on thin layer plates and develop the plates on chloroform:methanol (9:1).

Detect the antibiotic components by observation of spot color after exposing the developed plates to iodine vapors and by bioautography of a duplicate plate against *S. aureus*.

Obtain component 3 by combining fractions 47 to 72. Remove the solvent by stripping to yield a residue. Dissolve the residue in chloroform:methanol (1:1, v/v) and then add a mixture of ether:hexane (6:4, v/v) until a precipitate forms. Filter the precipitate and dry in a vacuum to 1.2 g of antibiotic 13-384 component 3.

EXAMPLE 5

Separation of Antibiotic 13-384 Component 3A

Dissolve 4.9 gm of antibiotic 13-384 in 1000 mL of ethyl acetate. Remove the insolubles by filtration. Wash the organic solution with water. Extract the ethyl acetate solution twice with 500 mL of 0.1N sulfuric acid. Combine the aqueous acidic phases and add sodium hydroxide until the pH is 9.5. Extract the aqueous alkaline solution twice with 1 liter of ethyl acetate. Combine the ethyl acetate extracts and remove the solvent by stripping. Dissolve the residue on 100 mL of ethyl ether and wash the solution with distilled water. Slowly evaporate the ether so as to allow antibiotic component 3A to crystallize from solution as long needles. Filter the product and dry in vacuum. Component 3A was examined by IR, UV, $^1H$ and $^{13}C$ NMR and mass spectrometry and was found to be identical to an authentic sample of chloraphenicol.

We claim:

1. A biologically pure culture of the microorganism *Micromonospora carbonacea* var *africana* having the identifying characteristics of NRRL 15099, said culture being capable of producing the antibiotic 13-384 complex in recoverable quantity upon fermentation, under aerobic conditions, in an aqueous nutrient medium containing assimilable sources of carbon and nitrogen.

* * * * *